US012157906B2

(12) United States Patent
Pel et al.

(10) Patent No.: US 12,157,906 B2
(45) Date of Patent: Dec. 3, 2024

(54) PROCESS FOR PRODUCING A FERMENTATION BROTH

(71) Applicant: VERSALIS S.P.A., San Donato Milanese (IT)

(72) Inventors: Herman Jan Pel, Echt (NL); Maaike Appeldoorn, Echt (NL); Rolf Poldermans, Echt (NL)

(73) Assignee: VERSALIS S.P.A., San Donato Milanese (IT)

( * ) Notice: Subject to any disclaimer, the term of this patent is extended or adjusted under 35 U.S.C. 154(b) by 77 days.

(21) Appl. No.: 17/437,566

(22) PCT Filed: Mar. 11, 2020

(86) PCT No.: PCT/EP2020/056406
§ 371 (c)(1),
(2) Date: Sep. 9, 2021

(87) PCT Pub. No.: WO2020/182843
PCT Pub. Date: Sep. 17, 2020

(65) Prior Publication Data
US 2022/0186264 A1  Jun. 16, 2022

(30) Foreign Application Priority Data
Mar. 12, 2019 (EP) .................................... 19162388

(51) Int. Cl.
*C12P 1/02* (2006.01)
*C12N 1/14* (2006.01)
*C12N 9/24* (2006.01)

(52) U.S. Cl.
CPC .................. *C12P 1/02* (2013.01); *C12N 1/14* (2013.01); *C12N 9/24* (2013.01)

(58) Field of Classification Search
None
See application file for complete search history.

(56) References Cited

U.S. PATENT DOCUMENTS

| | | | |
|---|---|---|---|
| 5,275,944 A | 1/1994 | Himmel et al. | |
| 5,457,046 A | 10/1995 | Woldike et al. | |
| 5,536,655 A | 7/1996 | Thomas et al. | |
| 5,648,263 A | 7/1997 | Schulein et al. | |
| 5,686,593 A | 11/1997 | Woldike et al. | |
| 6,022,725 A | 2/2000 | Fowler et al. | |
| 6,982,159 B2 | 1/2006 | Dunn-Coleman et al. | |
| 7,005,289 B2 | 2/2006 | Dunn-Coleman et al. | |
| 7,045,332 B2 | 5/2006 | Dunn-Coleman et al. | |
| 7,514,110 B1 | 4/2009 | Van Den Hombergh et al. | |
| 7,759,102 B2 | 7/2010 | Van Den Hombergh et al. | |
| 9,121,013 B2 | 9/2015 | Schooneveld-Bergmans et al. | |
| 9,133,448 B2 | 9/2015 | Sagt et al. | |
| 9,163,224 B2 | 10/2015 | Sagt et al. | |
| 9,260,704 B2 | 2/2016 | Schooneveld-Bergmans et al. | |
| 9,441,214 B2 | 9/2016 | Schooneveld-Bergmans et al. | |
| 9,988,615 B2 | 6/2018 | Los et al. | |
| 10,316,305 B2 | 6/2019 | Los et al. | |
| 10,435,718 B2 * | 10/2019 | Smits | ...................... C12P 19/02 |
| 10,655,115 B2 | 5/2020 | Los et al. | |
| 10,865,427 B2 | 12/2020 | Smits et al. | |
| 11,319,560 B2 | 5/2022 | Smits et al. | |
| 11,447,759 B2 | 9/2022 | Los et al. | |
| 2004/0102619 A1 | 5/2004 | Dunn-Coleman et al. | |
| 2006/0258554 A1 | 11/2006 | Dunn-Coleman et al. | |
| 2008/0274886 A1 | 11/2008 | Van Den Homberg et al. | |
| 2012/0276567 A1 | 11/2012 | Los et al. | |
| 2013/0061354 A1 | 3/2013 | Sagt et al. | |
| 2013/0095531 A1 | 4/2013 | Schooneveld-Bergmans | |
| 2013/0095553 A1 | 4/2013 | Schooneveld-Bergmans et al. | |
| 2013/0104264 A1 | 4/2013 | Schooneveld-Bergmans et al. | |
| 2013/0145501 A1 | 6/2013 | Sagt et al. | |
| 2015/0118717 A1 | 4/2015 | Wang et al. | |
| 2015/0361408 A1 | 12/2015 | Los et al. | |
| 2017/0247722 A1 | 8/2017 | Smits et al. | |
| 2018/0010154 A1 | 1/2018 | Smits | |
| 2018/0245059 A1 | 8/2018 | Los et al. | |
| 2019/0136213 A1 | 5/2019 | Los et al. | |
| 2019/0284594 A1 | 9/2019 | Bevers et al. | |
| 2019/0382805 A1 | 12/2019 | Smits et al. | |
| 2020/0190495 A1 | 6/2020 | Los et al. | |
| 2020/0347422 A1 * | 11/2020 | Appeldoorn | ............ C12P 19/02 |
| 2021/0002676 A1 | 1/2021 | Smits et al. | |

FOREIGN PATENT DOCUMENTS

| | | |
|---|---|---|
| CN | 102597213 A | 7/2012 |
| CN | 103436509 A | 12/2013 |
| CN | 107075533 A | 8/2017 |
| EP | 1468093 A1 | 10/2004 |
| EP | 1499708 A1 | 1/2005 |
| WO | 1991/05039 A1 | 4/1991 |
| WO | 1993/15186 A1 | 8/1993 |

(Continued)

OTHER PUBLICATIONS

Lu et al. (Biotechnology and Bioengineering, vol. 110, No. 8, pp. 2123-2130 Aug. 2013).*
Kovacs et al. (Process Biochemistry vol. 44, pp. 1323-1329, 2009).*
PCT International Search Report for PCT/EP2020/056406, mailed Apr. 20, 2020.
Alazi et al., "Modulating Transcriptional Regulation of Plant Biomass Degrading Enzyme Networks for Rational Design of Industrial Fungal Strains," Frontiers in Bioengineering and Biotechnology, (2018), vol. 6: 1-12.
Taherzadeh-Ghahfarokhi et al., "Optimizing the combination of conventional carbonaceous additives of culture media to produce lignocellulose-degrading enzymes by Trichoderma reesei in solid state fermentation of agricultural residues," Renewable Energy, (2018), vol. 131: 946-955.

(Continued)

*Primary Examiner* — Richard G Hutson
(74) *Attorney, Agent, or Firm* — McBee Moore & Vanik, IP, LLC

(57) ABSTRACT

The invention relates to a process for producing a fermentation broth by culturing a microorganism.

9 Claims, No Drawings

(56) References Cited

FOREIGN PATENT DOCUMENTS

| | | |
|---|---|---|
| WO | 1994/21785 A1 | 9/1994 |
| WO | 1996/02551 A1 | 2/1996 |
| WO | 1998/13465 A1 | 4/1998 |
| WO | 1998/015619 A1 | 4/1998 |
| WO | 1998/015633 A1 | 4/1998 |
| WO | 1999/06574 A1 | 2/1999 |
| WO | 1999/10481 A2 | 3/1999 |
| WO | 1999/025847 A2 | 5/1999 |
| WO | 1999/031255 A2 | 6/1999 |
| WO | 2000/70031 A1 | 11/2000 |
| WO | 2001/70998 A1 | 9/2001 |
| WO | 2002/24926 A1 | 3/2002 |
| WO | 02/095014 A2 | 11/2002 |
| WO | 2002/101078 A2 | 12/2002 |
| WO | 2003/027306 A2 | 4/2003 |
| WO | 2003/052054 A2 | 6/2003 |
| WO | 2003/052056 A2 | 6/2003 |
| WO | 2003/052057 A2 | 6/2003 |
| WO | 2003/052118 A2 | 6/2003 |
| WO | 2003/062430 A1 | 7/2003 |
| WO | 2003/095627 A1 | 11/2003 |
| WO | 2004/016760 A2 | 2/2004 |
| WO | 2004/043980 A2 | 5/2004 |
| WO | 2004/048592 A2 | 6/2004 |
| WO | 2005/001036 A2 | 1/2005 |
| WO | 2005/001065 A2 | 1/2005 |
| WO | 2005/028636 A2 | 3/2005 |
| WO | 2005/047499 A1 | 5/2005 |
| WO | 2005/074647 A2 | 8/2005 |
| WO | 2005/074656 A2 | 8/2005 |
| WO | 2005/093050 A2 | 10/2005 |
| WO | 2005/093073 A1 | 10/2005 |
| WO | 2006/009434 A1 | 1/2006 |
| WO | 2006/074005 A2 | 7/2006 |
| WO | 2006/078256 A2 | 7/2006 |
| WO | 2006/114094 A1 | 11/2006 |
| WO | 2006/117432 A1 | 11/2006 |
| WO | 2007/019442 A2 | 2/2007 |
| WO | 2007/071818 A1 | 6/2007 |
| WO | 2007/071820 A1 | 6/2007 |
| WO | 2007/089290 A2 | 8/2007 |
| WO | 2008/008070 A2 | 1/2008 |
| WO | 2008/008793 A2 | 1/2008 |
| WO | 2008/041840 A1 | 4/2008 |
| WO | 2008/057637 A2 | 5/2008 |
| WO | 2008/148131 A1 | 12/2008 |
| WO | 2009/011591 A2 | 1/2009 |
| WO | 2009/042846 A1 | 4/2009 |
| WO | 2009/068565 A1 | 6/2009 |
| WO | 2009/073383 A1 | 6/2009 |
| WO | 2009/076122 A1 | 6/2009 |
| WO | 2009/079210 A2 | 6/2009 |
| WO | 2009/085859 A2 | 7/2009 |
| WO | 2009/085864 A2 | 7/2009 |
| WO | 2009/085868 A1 | 7/2009 |
| WO | 2009/085935 A2 | 7/2009 |
| WO | 2009/127729 A1 | 10/2009 |
| WO | 2010/000888 A1 | 1/2010 |
| WO | 2010/014706 A1 | 2/2010 |
| WO | 2010/014880 A1 | 2/2010 |
| WO | 2010/053838 A1 | 5/2010 |
| WO | 2010/065448 A1 | 6/2010 |
| WO | 2010/065830 A1 | 6/2010 |
| WO | 2010/108918 A1 | 9/2010 |
| WO | 2010/122141 A1 | 10/2010 |
| WO | 2010/126772 A1 | 11/2010 |
| WO | 2010/138754 A1 | 12/2010 |
| WO | 2011/005867 A1 | 1/2011 |
| WO | WO-2011000949 A1 * | 1/2011 ........... C12N 9/2437 |
| WO | 2011/035027 A2 | 3/2011 |
| WO | 2011/035029 A1 | 3/2011 |
| WO | 2011/039319 A1 | 4/2011 |
| WO | 2011/041397 A1 | 4/2011 |
| WO | 2011/041405 A1 | 4/2011 |
| WO | 2011/041504 A1 | 4/2011 |
| WO | 2011/057083 A1 | 5/2011 |
| WO | 2011/057140 A1 | 5/2011 |
| WO | 2009/073709 A1 | 6/2011 |
| WO | 2011/098580 A1 | 8/2011 |
| WO | 2012/000886 A1 | 1/2012 |
| WO | 2012/000890 | 1/2012 |
| WO | 2012/000890 A1 | 1/2012 |
| WO | 2012/000892 A1 | 1/2012 |
| WO | 2012/044915 A2 | 4/2012 |
| WO | 2014/118360 A2 | 8/2014 |
| WO | 2014/130812 A1 | 8/2014 |
| WO | 2018/096019 A1 | 5/2018 |
| WO | 2019/086369 A1 | 5/2019 |
| WO | 2003/052055 A2 | 6/2023 |

OTHER PUBLICATIONS

Ellila et al., "Development of a low-cost cellulase production process using Trichoderma reesei for Brazilian piorefineries," Biotechnol Biofuels, (2017), vol. 10: 1-17.

Martinez et al., "The two Rasamsonia emersonii a-glucuronidases, ReGH67 and ReGH115, show a different mode-of-action towards glucuronoxylan and glucuronoxylo-oligosaccharides," Biotechnol Biofuels, (2016), vol. 9: 1-10.

Moloney et al., "Cellulose Hydrolysis by the Cellulases Produced by Talaromyces emersonii when Grown on Different Inducing Substrates," Biotechnology and Bioengineering, (1983), vol. XXV: 1169-1173.

Li et al., "Optimization of cellulolytic enzyme components through engineering Trichoderma reesei and on-site fermentation using the soluble inducer for cellulosic ethanol production from corn stover," Biotechnol Biofuels, (2018), vol. 11: 1-14.

Adsul et al., "Designing a cellulolytic enzyme cocktail for the efficient and economical conversion of lignocellulosic biomass to biofuels," Enzyme and Microbial Technology, (2020), vol. 133: 109442.

Isaksen et al., "A C4-oxidizing Lytic Polysaccharide Monooxygenase Cleaving Both Cellulose and Cello-oligosaccharides" Journal of Biological Chemistry, vol. 289, No. 5, p. 2632-2642; The American Society for Biochemistry and Molecular Biology, Inc.

Filamentous fungi include all filamentous forms of the subdivision Eumycota and Oomycota (as defined by Hawksworth et al., In, Ainsworth and Bisby's Dictionary of The Fungi, 8th edition, 1995, CAB International, University, Press, Cambridge, UK.

* cited by examiner

PROCESS FOR PRODUCING A FERMENTATION BROTH

CROSS-REFERENCE TO RELATED APPLICATIONS

This application is the National Stage entry of International Application No. PCT/EP2020/056406, filed 11 Mar. 2020, which claims priority to European Patent Application No. 19162388.3, filed 12 Mar. 2019.

BACKGROUND

Field

The invention relates to a process for producing a fermentation broth by culturing a microorganism.

Description of Related Art

In recent years, yeasts and fungi have become attractive options for expressing cellulolytic and hemicellulolytic enzymes, as they can be easily grown at a large scale in simple media, which allows low production costs.

In particular filamentous fungi such as *Aspergillus* and *Trichoderma* have been developed into expression platforms for screening and production. Their ability to express native and heterologous enzymes to high levels, makes them well-suited for the large-scale production of enzymes.

Molloney et al. (1983), Biotechnology and Bioengineering, Vol. XXV, pages 1169-1173 describes hydrolysis of cellulose by cellulases produced by *Talaromyces emersonii* when grown on different inducing substrates. Ellilä et al. (2017), Biotechnology for Biofuels, Vol. 10, pages 1-17 describes a simple and cost-efficient cellulase production process using engineered *Trichoderma reesei* strains.

Although a considerable amount of research work has been performed on cellulolytic and hemicellulolytic enzymes and their production by filamentous fungi, the high cost of enzymes still restricts their use and commercialization in sectors such as the bioenergy sector. Advancements in biotechnology such as screening and finding of new microorganisms and enzymes could lower the production costs of cellulolytic and hemicellulolytic enzymes. However, next to the optimization of the enzymes themselves, optimization of process design is a crucial tool to reduce overall costs of the production of enzymes. For example, commercially cheaper sources of carbohydrates and modified fermentation conditions could lead to more cost-effective production of cellulolytic and hemicellulolytic enzyme compositions. For economic reasons, it is therefore desirable to include new and innovative process configurations aimed at reducing overall production costs.

SUMMARY

An object of the invention is to provide an improved production process for whole fermentation broths comprising cellulolytic and/or hemicellulolytic enzymes. In particular, the object of the invention is to provide an improved production process for whole fermentation broths by fungi. Optimization and improvement lie in culturing a fungus in the presence of an inducer to produce a first whole fermentation broth and culturing a fungus in the absence of an inducer to produce a second whole fermentation broth and combining the first and second whole fermentation broth.

DETAILED DESCRIPTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element. The term "enzyme" as used herein means one or more enzymes.

Described herein is a process for producing a mixed whole fermentation broth comprising cellulolytic and/or hemicellulolytic enzymes, wherein the process comprises the step of (i) culturing a filamentous fungus in the presence of an inducer to produce a first whole fermentation broth comprising cellulolytic and/or hemicellulolytic enzymes, (ii) culturing a filamentous fungus in the absence of an inducer to produce a second whole fermentation broth comprising cellulolytic and/or hemicellulolytic enzymes, and combining the first and second first whole fermentation broth to produce a mixed whole fermentation broth comprising cellulolytic and/or hemicellulolytic enzymes. Optionally, the mixed whole fermentation broth can be recovered. Optionally, even one or more additional whole fermentation broths (i.e. a third, fourth, fifth, sixth etc whole fermentation broth), produced either by culturing a filamentous fungus in the presence of an inducer or by culturing a filamentous fungus in the absence of an inducer can be combined with the first, second and/or mixed whole fermentation broth. In other words, the whole fermentation broths as described herein may be supplemented with at least another whole fermentation broth. The other whole fermentation broth may be derived from the same type of fungus or from another type of fungus. As used herein "broth comprising cellulolytic and/or hemicellulolytic enzymes" means "broth comprising one or more cellulolytic and/or hemicellulolytic enzymes".

In an embodiment the mixed whole fermentation broth comprises a ratio of first whole fermentation broth to second whole fermentation broth in the range from 99% (w/w) to 1% (w/w)-70% (w/w) to 30% (w/w), 95% (w/w) to 5% (w/w)-75% (w/w) to 25% (w/w), 90% (w/w) to 10% (w/w)-80% (w/w) to 20% (w/w). In an embodiment "whole fermentation broth comprising cellulolytic and/or hemicellulolytic enzymes" means that the whole fermentation broth comprises at least one cellulolytic and/or hemicellulolytic enzyme. In an preferred embodiment the whole fermentation broth comprises more than one cellulolytic and/or hemicellulolytic enzyme.

The filamentous fungi are cultured under conditions conducive for production of the whole fermentation broths comprising cellulolytic and/or hemicellulolytic enzymes. "Conducive for production of the whole fermentation broths comprising cellulolytic and/or hemicellulolytic enzymes" as used herein means a suitable growth and production medium comprising carbon and nitrogen sources and inorganic salts, a suitable growth and production temperature in the range of 20° C. to 60° C., a suitable growth and production pH in the range of 3 to 8, a culturing time of 3 weeks or less.

The step of culturing a filamentous fungus in the presence or absence of an inducer to produce a first or second whole fermentation broth comprising cellulolytic and/or hemicellulolytic enzymes as described herein can be preceded by a process for propagating the filamentous fungus. Propagation may comprise several steps in shake flasks, small containers and large containers.

In an embodiment the container(s) used in the process for producing a mixed whole fermentation broth comprising cellulolytic and/or hemicellulolytic enzymes as described herein have a volume of at least 1 m$^3$. Preferably, the containers have a volume of at least 1 m$^3$, at least 2 m$^3$, at least 3 m$^3$, at least 4 m$^3$, at least 5 m$^3$, at least 6 m$^3$, at least 7 m$^3$, at least 8 m$^3$, at least 9 m$^3$, at least 10 m$^3$, at least 15 m$^3$, at least 20 m$^3$, at least 25 m$^3$, at least 30 m$^3$, at least 35 m$^3$, at least 40 m$^3$, at least 45 m$^3$, at least 50 m$^3$, at least 60 m$^3$, at least 70 m$^3$, at least 75 m$^3$, at least 80 m$^3$, at least 90 m$^3$. In general, the container(s) will be smaller than 1000 m$^3$.

In an embodiment the container used for culturing a filamentous fungus in the presence of an inducer to produce a first whole fermentation broth comprising cellulolytic and/or hemicellulolytic enzymes is the same container as the container used for culturing a filamentous fungus in the absence of an inducer to produce a second whole fermentation broth comprising cellulolytic and/or hemicellulolytic enzymes. In an embodiment the container used for culturing a filamentous fungus in the presence of an inducer to produce a first whole fermentation broth comprising cellulolytic and/or hemicellulolytic enzymes is different from the container used for culturing a filamentous fungus in the absence of an inducer to produce a second whole fermentation broth comprising cellulolytic and/or hemicellulolytic enzymes. In case the containers are different, they may have the same volume, but may also have a different volume.

In an embodiment the container used for combining the first and second first whole fermentation broth to produce a mixed whole fermentation broth comprising cellulolytic and/or hemicellulolytic enzymes is the same container as the container used for culturing a filamentous fungus in the presence and/or absence of an inducer to produce a first and/or second whole fermentation broth comprising cellulolytic and/or hemicellulolytic enzymes. In an embodiment the container used for combining the first and second whole fermentation broth to produce a mixed whole fermentation broth comprising cellulolytic and/or hemicellulolytic enzymes is different from the container used for culturing a filamentous fungus in the presence and/or absence of an inducer to produce a first and/or second whole fermentation broth comprising cellulolytic and/or hemicellulolytic enzymes.

In an embodiment the step of culturing a filamentous fungus in the presence of an inducer to produce a first whole fermentation broth comprising cellulolytic and/or hemicellulolytic enzymes is done in a first container, the step of culturing a filamentous fungus in the absence of an inducer to produce a second whole fermentation broth comprising cellulolytic and/or hemicellulolytic enzymes is done in a second container and the step of combining the first and second first whole fermentation broth to produce a mixed whole fermentation broth comprising cellulolytic and/or hemicellulolytic enzymes is done in a third container.

In an embodiment the filamentous fungus is cultured in a fed-batch culture, a batch culture, a continuous culture or any combination thereof. Preferably, the fungus is cultured in a fed-batch culture. A person skilled in the art is well aware of the various modes of culturing and its conditions.

In an embodiment the culturing is conducted under aerobic conditions. A person skilled in the art is well aware of container designs for aerobic cultivation such as for instance stirred containers and bubble columns.

In an embodiment one or more whole fermentation broths are (partially) purified. Methods for (partial) purification are known to the skilled artisan and include, but are not limited to, biomass removal, ultrafiltration and chromatography.

In a preferred embodiment the whole fermentation broths are not (partially) purified. In an embodiment the whole fermentation broths are fungal whole fermentation broths, preferably filamentous fungal whole fermentation broths.

The first whole fermentation broth can be prepared by culturing a non-recombinant and/or recombinant fungus. The second whole fermentation broth can be prepared by culturing a non-recombinant and/or recombinant fungus. In an embodiment the fungus is a recombinant fungus comprising one or more genes which can be homologous or heterologous to the fungus. In an embodiment, the fungus is a recombinant fungus comprising one or more genes which can be homologous or heterologous to the fungus wherein the one or more genes encode enzymes that can degrade a cellulosic substrate. In an embodiment the fungus is a non-recombinant fungus comprising one or more genes which are homologous to the fungus. In an embodiment, the fungus is a non-recombinant fungus comprising one or more genes which are homologous to the fungus wherein the one or more genes encode enzymes that can degrade a cellulosic substrate. The mixed whole fermentation broth may a mixture of whole fermentation broths of non-recombinant and/or recombinant fungi.

In an embodiment the fungus producing the first whole fermentation broth is different from the fungus producing the second whole fermentation broth. In an embodiment the fungus producing the first whole fermentation broth is identical to the fungus producing the second whole fermentation broth.

Preferably, the cells are killed in the whole fermentation broth. The whole fermentation broth may contain organic acid(s) (used for killing the cells), killed cells and/or cell debris, and culture medium. The whole fermentation broths as described herein comprise cellulolytic and/or hemicellulolytic enzymes.

The fungus may be altered to improve or to make the enzymes. For example, the fungus may be mutated by classical strain improvement procedures or by recombinant DNA techniques. Therefore, the fungi mentioned herein can be used as such to produce the enzymes or may be altered to increase the production or to produce altered enzymes which might include heterologous enzymes, e.g. cellulases and/or hemicellulases, thus enzymes that are not originally produced by that fungus. Preferably, a fungus, more preferably a filamentous fungus, is used to produce the enzymes. The enzymes produced by the fungus according to the processes as described herein are preferably cellulolytic and/or hemicellulolytic enzymes. Advantageously, a thermophilic or thermotolerant filamentous fungus is used.

Generally, the fungi are cultivated in a cell culture medium suitable for production of the cellulolytic and/or hemicellulolytic enzymes. The enzymes are capable of hydrolyzing a cellulosic substrate. Suitable culture media are known in the art. The whole fermentation broth can be prepared by growing the fungi to stationary phase and maintaining the fungi under limiting carbon conditions for a period of time sufficient to express the enzyme. Once the enzyme of interest is secreted by the fungi into the fermentation medium, the whole fermentation broth can be used. The whole fermentation broth may comprise fungi. In some embodiments, the whole fermentation broth comprises the unfractionated contents of the fermentation materials derived at the end of the fermentation. Typically, the whole fermentation broth comprises the spent culture medium and cell debris present after the fungi is grown to saturation, incubated under carbon-limiting conditions to allow protein synthesis. In some embodiments, the whole fermentation broth comprises the spent cell culture medium, extracellular enzymes and fungi. In some embodiments, the fungi present in whole fermentation broth can be lysed, permeabilized, or killed using methods known in the art to produce a cell-killed whole fermentation broth. In an embodiment, the whole fermentation broth is a cell-killed whole fermentation broth, wherein the whole fermentation broth containing the fungi cells are lysed or killed. In some embodiments, the cells are killed by lysing the fungi by chemical and/or pH treatment to generate the cell-killed whole broth of a fermentation of the fungi. In some embodiments, the cells are killed by lysing the fungi by chemical and/or pH treatment and adjusting the pH of the cell-killed fermentation mix to a suitable pH. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

In an embodiment one of the whole fermentation broths comprising cellulolytic and/or hemicellulolytic enzymes is produced by culturing a filamentous fungus in the presence of an inducer, while the other of the whole fermentation broths comprising cellulolytic and/or hemicellulolytic enzymes is produced by culturing a filamentous fungus in the absence of an inducer. This means that at least during production of one of the whole fermentation broths a filamentous fungus is cultured in the presence of an inducer and at least during production of one of the other whole fermentation broths a filamentous fungus is cultured in the absence of an inducer. As used herein "in the presence of an inducer" means that inducer is added before and/or during culturing of the filamentous fungus to the medium wherein the culturing takes place. In an embodiment the inducer is added in an amount of 10% (w/v)-0.01% (w/v). As used herein "in the absence of an inducer" means that no or only a little amount of inducer is added before and/or during culturing of the filamentous fungus to the medium wherein the culturing takes place. "No or only a little amount" as used herein means that the inducer is added in an amount of 0.1% (w/v) or lower, preferably 0.01% (w/v) or lower, even more preferably lower than 0.01% (w/v).

In an embodiment the filamentous fungus is cultured in step (i) of the herein described processes in the presence of an inducer. Enzyme induction is a process where an enzyme is manufactured in response to the presence of a specific molecule. This molecule is herein termed an inducer. Typically, an inducer is a compound that the enzyme acts upon or that is produced by the enzyme. The inducer is selected from the group consisting of cellulose, carboxymethylcellulose (CMC), xylan, xylose, gentiobiose, sophorose, lactose, glycerol, glucose, sorbitol, cellobiose, xylobiose, galactose, laminaribiose, maltose, fructose, mannitol, arabinose, arabinitolo, mannose, sorbose, a mixture of disaccharides prepared from glucose by incubating glucose with a transglycosylating beta-glucosidase, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular polypeptides (such as cellulolytic and/or hemicellulolytic enzymes), and microbial, preferably non-viable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or anti-microbial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment the whole fermentation broth may be supplemented with one or more enzymes. In an embodiment the whole fermentation broth may be supplemented with one or more enzyme activities that are not expressed endogenously, or expressed at relatively low level by the fungi, to improve the degradation of the cellulosic substrate, for example, to fermentable sugars such as glucose or xylose. The supplemental enzyme(s) can be added as a supplement to the whole fermentation broth and the enzyme(s) may be a component of a separate whole fermentation broth, or may be purified, or minimally recovered and/or purified.

In an embodiment the whole fermentation broth comprises a whole fermentation broth of a fermentation of a recombinant fungus overexpressing one or more enzymes (such as one or more cellulolytic and/or hemicellulolytic enzymes). In an embodiment the whole fermentation broth comprises a whole fermentation broth of a fermentation of a recombinant fungus overexpressing one or more enzymes (such as cellulolytic and/or hemicellulolytic enzymes) to improve the degradation of the cellulosic substrate. Alternatively, the whole fermentation broth can comprise a mixture of a whole fermentation broth of a fermentation of a non-recombinant fungus and a recombinant fungus overexpressing one or more enzymes (such as cellulolytic and/or hemicellulolytic enzymes). Alternatively, the whole fermentation broth can comprise a mixture of a whole fermentation broth of a fermentation of a non-recombinant fungus and a recombinant fungus overexpressing one or more enzymes (such as cellulolytic and/or hemicellulolytic enzymes) to improve the degradation of the cellulosic substrate. In an embodiment, the whole fermentation broth comprises a whole fermentation broth of a fermentation of a fungus overexpressing beta-glucosidase. Alternatively, the whole fermentation broth can comprise a mixture of a whole fermentation broth of a fermentation of a non-recombinant fungus and a whole fermentation broth of a fermentation of a recombinant fungus overexpressing a beta-glucosidase.

In an embodiment the filamentous fungus is selected from the group of genera consisting of *Acremonium, Agaricus, Aspergillus, Aureobasidium, Beauvaria, Cephalosporium, Ceriporiopsis, Chaetomium paecilomyces, Chrysosporium,*

*Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes pleurotus, Trichoderma* and *Trichophyton*. In a preferred embodiment the filamentous fungus belongs to the genus *Rasamsonia, Penicillium, Trichoderma* or *Aspergillus*.

As described before, the fungus producing the first whole fermentation broth can be different from the fungus producing the second whole fermentation broth. The fungus producing the first whole fermentation broth can also be identical to the fungus producing the second whole fermentation broth. In an embodiment the fungus producing the first whole fermentation broth can be from a different genus than the fungus producing the second whole fermentation broth. In an embodiment the fungus producing the first whole fermentation broth can be from the same genus as the fungus producing the second whole fermentation broth. In an embodiment the fungus producing the first whole fermentation broth can be from the same genus as the fungus producing the second whole fermentation broth, but from a different species than the fungus producing the second whole fermentation broth. In an embodiment the fungus producing the first whole fermentation broth can be from the same species as the fungus producing the second whole fermentation broth.

"Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

*Rasamsonia* is a new genus comprising thermotolerant and thermophilic *Talaromyces* and *Geosmithia* species (J. Houbraken et al., vida supra). Based on phenotypic, physiological and molecular data, Houbraken et al. proposed to transfer the species *Talaromyces emersonii, Talaromyces byssochlamydoides, Talaromyces eburneus, Geosmithia argillacea* and *Geosmithia cylindrospora* to *Rasamsonia* gen. nov. Preferred fungi are *Rasamsonia byssochlamydoides, Rasamsonia emersonii, Thermomyces lenuginosus, Talaromyces thermophilus, Thermoascus crustaceus, Thermoascus thermophilus* and *Thermoascus aurantiacus*, with *Rasamsonia emersonii* being most preferred. *Talaromyces emersonii, Penicillium Geosmithia emersonii* and *Rasamsonia emersonii* are used interchangeably herein.

In an embodiment the enzymes in the whole fermentation broths produced by the processes as described herein have cellulosic material degrading and/or cellulose hydrolysing activity. In other words, the enzymes that are produced by the fungus have cellulosic material degrading and/or cellulose hydrolysing activity. In other words, the enzymes are cellulolytic and/or hemicellulolytic enzymes.

In an embodiment the enzymes are native to the fungus. In another embodiment the enzyme is heterologous to the fungus. The term "heterologous" as used herein refers to an enzyme that is not naturally occurring in a host cell. It may be a variant of a native enzyme, but may also be an enzyme of another species. For example, an enzyme of *Rasamsonia*, when expressed by *Aspergillus*, is considered to be heterologous. An enzyme of *Rasamsonia emersonii*, when expressed by *Rasamsonia byssochlamydoides*, is also considered to be heterologous. An enzyme of a specific *Rasamsonia emersonii* strain when expressed by another *Rasamsonia emersonii* strain is however considered to be native. When a synthetic gene is introduced into a strain and this gene encodes for an enzyme that is identical to the native enzyme found in the strain, the enzyme encoded by the synthetic gene is also considered to be native.

In an embodiment the fungus is overexpressing the enzyme. The fungus may comprise more than one copy of a polynucleotide encoding the native or heterologous enzyme. Typically, the enzyme is a cellulase, hemicellulase and/or pectinase.

In an embodiment the fungus may also produce two or more, for example, three, four, five, six, seven, eight, nine or even more enzymes. Some enzymes may be native while others are heterologous. In an embodiment the fungus produces at least two cellulases. The at least two cellulases may contain the same or different activities. The fungus may produce a cellulase and/or a hemicellulase and/or a pectinase from a source other than the fungus. In another embodiment after production by the fungus, the produced enzyme may be combined with one or more other enzymes. The combination of enzymes can then for instance be used in a process for producing a sugar product from cellulosic material or in a process for producing a fermentation product from cellulosic material as described herein.

In an embodiment the first whole fermentation broth comprises a cellobiohydrolase I, a cellobiohydrolase II, an endoglucanase, a beta-glucosidase, a beta-xylosidase, an endoxylanase, a lytic polysaccharide monooxygenase, an acetyl xylan esterase or any combination thereof.

In an embodiment the second whole fermentation broth comprises a cellobiohydrolase I, a cellobiohydrolase II, an endoglucanase, a beta-glucosidase, a beta-xylosidase, an endoxylanase, a lytic polysaccharide monooxygenase, an acetyl xylan esterase or any combination thereof.

In an embodiment the enzymes in the first whole fermentation broth differ from the enzymes in the second whole fermentation broth. In an embodiment the enzymes in the first and second whole fermentation are the same. In an embodiment one or more of the enzymes in the first and second whole fermentation are the same and one or more differ. In an embodiment the enzymes in the first and second whole fermentation are the same, but their amount based on total protein content differs. For example, both the first and second whole fermentation broth may comprise a cellobiohydrolase, but the amount of the cellobiohydrolase based on total protein content differs between the two broths.

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

In an embodiment a whole fermentation broth as described herein comprises a beta-glucosidase from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus*, *Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment even a bacterial beta-glucosidase can be used. In another embodiment the beta-glucosidase is derived from *Thielavia terrestris* (WO 2011/035029) or *Trichophaea saccata* (WO 2007/019442). In a preferred embodiment a whole fermentation broth comprises a beta-glucosidase from *Rasamsonia*, such as *Rasamsonia emersonii* (see WO 2012/000886).

As used herein, endoglucanases are enzymes which are capable of catalyzing the endohydrolysis of 1,4-β-D-glucosidic linkages in cellulose, lichenin or cereal β-D-glucans. They belong to EC 3.2.1.4 and may also be capable of hydrolyzing 1,4-linkages in β-D-glucans also containing 1,3-linkages. Endoglucanases may also be referred to as cellulases, avicelases, β-1,4-endoglucan hydrolases, β-1,4-glucanases, carboxymethyl cellulases, celludextrinases, endo-1,4-β-D-glucanases, endo-1,4-β-D-glucanohydrolases or endo-1,4-β-glucanases.

In an embodiment the endoglucanase comprises a GH5 endoglucanase and/or a GH7 endoglucanase. This means that at least one of the endoglucanases in the whole fermentation broth may be a GH5 endoglucanase or a GH7 endoglucanase. In case there are more endoglucanases in the whole fermentation broth, these endoglucanases can be GH5 endoglucanases, GH7 endoglucanases or a combination of GH5 endoglucanases and GH7 endoglucanases. In a preferred embodiment the endoglucanase comprises a GH5 endoglucanase.

In an embodiment a whole fermentation broth as described herein comprises an endoglucanase from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; from *Humicola*, such as *Humicola grisea* var. thermoidea or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum*; and/or from *Chrysosporium*, such as a strain of *Chrysosporium lucknowense*. In a preferred embodiment the endoglucanase is from *Rasamsonia*, such as a strain of *Rasamsonia emersonii* (see WO 01/70998). In an embodiment even a bacterial endoglucanase can be used including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

In an embodiment a whole fermentation broth as described herein comprises a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812; from *Trichoderma*, such as *Trichoderma reesei*; from *Chaetomium*, such as *Chaetomium thermophilum*; from *Talaromyces*, such as *Talaromyces leycettanus* or from *Penicillium*, such as *Penicillium emersonii*. In a preferred embodiment a whole fermentation broth comprises a cellobiohydrolase I from *Rasamsonia*, such as *Rasamsonia emersonii* (see WO 2010/122141).

In an embodiment a whole fermentation broth as described herein comprises a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Talaromyces*, such as *Talaromyces leycettanus*, or from *Thielavia*, such as *Thielavia terrestris*, such as cellobiohydrolase II CEL6A from *Thielavia terrestris*. In a preferred embodiment a whole fermentation broth comprises a cellobiohydrolase II from *Rasamsonia*, such as *Rasamsonia emersonii* (see WO 2011/098580).

As used herein, lytic polysaccharide monooxygenases are enzymes that have recently been classified by CAZy in family AA9 (Auxiliary Activity Family 9) or family AA10 (Auxiliary Activity Family 10). Ergo, there exist AA9 lytic polysaccharide monooxygenases and AA10 lytic polysaccharide monooxygenases. Lytic polysaccharide monooxygenases are able to open a crystalline glucan structure and enhance the action of cellulases on lignocellulose substrates. They are enzymes having cellulolytic enhancing activity. Lytic polysaccharide monooxygenases may also affect cellooligosaccharides. According to the latest literature, (see Isaksen et al., Journal of Biological Chemistry, vol. 289, no. 5, p. 2632-2642), proteins named GH61 (glycoside hydrolase family 61 or sometimes referred to EGIV) are lytic polysaccharide monooxygenases. GH61 was originally classified as endoglucanase based on measurement of very weak endo-1,4-β-d-glucanase activity in one family member, but have recently been reclassified by CAZy in family AA9. CBM33 (family 33 carbohydrate-binding module) is also a lytic polysaccharide monooxygenase (see Isaksen et al, Journal of Biological Chemistry, vol. 289, no. 5, pp. 2632-2642). CAZy has recently reclassified CBM33 in the AA10 family.

In an embodiment the lytic polysaccharide monooxygenase comprises an AA9 lytic polysaccharide monooxygenase. This means that at least one of the lytic polysaccharide monooxygenases in the whole fermentation broth is an AA9 lytic polysaccharide monooxygenase. In an embodiment, all lytic polysaccharide monooxygenases in the whole fermentation broth are AA9 lytic polysaccharide monooxygenase.

In an embodiment a whole fermentation broth as described herein comprises a lytic polysaccharide monooxygenase from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable lytic polysaccharide monooxygenases include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). Other cellulolytic enzymes that may be comprised in the enzyme composition are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593, to name just a few. In a preferred embodiment, the lytic polysaccharide monooxygenase is from *Rasamsonia*, e.g. *Rasamsonia emersonii* (see WO 2012/000892).

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

In an embodiment the endoxylanase comprises a GH10 xylanase. This means that at least one of the endoxylanases in the whole fermentation broth as described herein is a GH10 xylanase. In an embodiment all endoxylanases in the whole fermentation broth as described herein are GH10 xylanases.

In an embodiment a whole fermentation broth as described herein comprises an endoxylanase from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), *Talaromyces leycettanus*, *Thermobifida fusca*, or *Trichophaea saccata* GH10 (see WO 2011/057083). In a preferred embodiment the whole fermentation broth as described herein comprises an endoxylanase from *Rasamsonia*, such as *Rasamsonia emersonii* (see WO 02/24926).

As used herein, beta-xylosidases (EC 3.2.1.37) are polypeptides which are capable of catalysing the hydrolysis of 1,4-β-D-xylans, to remove successive D-xylose residues from the non-reducing termini. Beta-xylosidases may also hydrolyze xylobiose. Beta-xylosidase may also be referred to as xylan 1,4-β-xylosidase, 1,4-β-D-xylan xylohydrolase, exo-1,4-β-xylosidase or xylobiase.

In an embodiment the beta-xylosidase comprises a GH3 beta-xylosidase. This means that at least one of the beta-xylosidases in the whole fermentation broth as described herein is a GH3 beta-xylosidase. In an embodiment all beta-xylosidases in the whole fermentation broth as described herein are GH3 beta-xylosidases.

In an embodiment a whole fermentation broth as described herein comprises a beta-xylosidase from *Neurospora crassa, Aspergillus fumigatus* or *Trichoderma reesei*. In a preferred embodiment the whole fermentation broth as described herein comprises a beta-xylosidase from *Rasamsonia*, such as *Rasamsonia emersonii* (see WO 2014/118360).

In an embodiment the whole fermentation broth as described herein may also comprises one or more of the below mentioned enzymes.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanase when the glucose residue whose reducing group is involved in the linkage to be hydrolysed is itself substituted at C-3. Alternative names include endo-1,3-beta-glucanase, laminarinase, 1,3-(1,3;1, 4)-beta-D-glucan 3 (4) glucanohydrolase. Substrates include laminarin, lichenin and cereal beta-D-glucans.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase. Examples of arabinofuranosidases that may be comprised in the whole fermentation broth as described herein include, but are not limited to, arabinofuranosidases from *Aspergillus niger, Humicola insolens* DSM 1800 (see WO 2006/114094 and WO 2009/073383) and *M. giganteus* (see WO 2006/114094).

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links. Examples of alpha-glucuronidases that may be comprised in the whole fermentation broth as described herein include, but are not limited to, alpha-glucuronidases from *Aspergillus clavatus, Aspergillus fumigatus, Aspergillus niger, Aspergillus terreus, Humicola insolens* (see WO 2010/014706), *Penicillium aurantiogriseum* (see WO 2009/068565) and *Trichoderma reesei*.

As used herein, an acetyl-xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin. Examples of acetylxylan esterases that may be comprised in the whole fermentation broth as described herein include, but are not limited to, acetylxylan esterases from *Aspergillus aculeatus* (see WO 2010/108918), *Chaetomium globosum*, *Chaetomium gracile*, *Humicola insolens* DSM 1800 (see WO 2009/073709), *Hypocrea jecorina* (see WO 2005/001036), *Myceliophtera thermophila* (see WO 2010/014880), *Neurospora crassa*, *Phaeosphaeria nodorum* and *Thielavia terrestris* NRRL 8126 (see WO 2009/042846). In a preferred embodiment the whole fermentation broth as described herein comprises an acetyl xylan esterase from *Rasamsonia*, such as *Rasamsonia emersonii* (see WO 2010/000888)

As used herein, a feruloyl esterase (EC 3.1.1.73) is any polypeptide which is capable of catalysing a reaction of the form: feruloyl-saccharide+$H_2O$=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin. Examples of feruloyl esterases (ferulic acid esterases) that may be comprised in the whole fermentation broth as described herein include, but are not limited to, feruloyl esterases form *Humicola insolens* DSM 1800 (see WO 2009/076122), *Neosartorya fischeri*, *Neurospora crassa*, *Penicillium aurantiogriseum* (see WO 2009/127729), and *Thielavia terrestris* (see WO 2010/053838 and WO 2010/065448).

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n $H_2O$=n methanol+pectate. The enzyme may also be known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: (1,4-α-D-galacturonide)$_n$+$H_2O$=(1,4-α-D-galacturonide)~-1+D-galacturonate. The enzyme may also be known as galacturan 1,4-α- galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes as described herein. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used is a ß-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucuronoside, for example β-glucuronoside to yield an alcohol. Many glucuronidases have been characterized and may be suitable for use, for example β-glucuronidase (EC 3.2.1.31), hyaluronо-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. As described herein, an expansin-like protein or swollenin-like protein may comprise one or both of such domains and/or may disrupt the structure of cell walls (such as disrupting cellulose structure), optionally without producing detectable amounts of reducing sugars.

A cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein may comprise one or both of such domains.

A catalase; the term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O + O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

The term "amylase" as used herein means enzymes that hydrolyze alpha-1,4-glucosidic linkages in starch, both in amylose and amylopectin, such as alpha-amylase (EC 3.2.1.1), beta-amylase (EC 3.2.1.2), glucan 1,4-alpha-glucosidase (EC 3.2.1.3), glucan 1,4-alpha-maltotetraohydrolase (EC 3.2.1.60), glucan 1,4-alpha-maltohexaosidase (EC 3.2.1.98), glucan 1,4-alpha-maltotriohydrolase (EC 3.2.1.116) and glucan 1,4-alpha-maltohydrolase (EC 3.2.1.133), and enzymes that hydrolyze alpha-1,6-glucosidic linkages, being the branch-points in amylopectin, such as pullulanase (EC 3.2.1.41) and limit dextinase (EC 3.2.1.142).

A whole fermentation broth produced by the fungus may comprise a member of each of the classes of enzymes mentioned above, several members of one enzyme class, or any combination of these enzymes classes or helper proteins (i.e. those proteins mentioned herein which do not have enzymatic activity per se, but do nevertheless assist in biomass degradation).

Herein is also described a mixed whole fermentation broth comprising cellulolytic and/or hemicellulolytic enzymes obtainable by a process for producing a mixed whole fermentation broth as described herein. Herein is also described a mixed whole fermentation broth obtainable by a process for producing a mixed whole fermentation broth as described herein and comprising cellulolytic and/or hemicellulolytic enzymes. The mixed whole fermentation broth comprising cellulolytic and/or hemicellulolytic enzymes may comprise any of the above features and embodiments. The mixed whole fermentation broth comprising cellulolytic and/or hemicellulolytic enzymes may comprise any of the above enzymes. In a preferred embodiment the mixed whole fermentation broth obtainable by a process for producing a mixed whole fermentation broth as described herein comprises a cellobiohydrolase I, a cellobiohydrolase II, an endoglucanase, a beta-glucosidase, an endoxylanase, a lytic polysaccharide monooxygenase and an acetyl xylan esterase. The mixed whole fermentation broth obtainable by a process for producing a mixed whole fermentation broth as described herein may also comprise a beta-xylosidase.

Herein is also described a process for the preparation of a sugar product from cellulosic material, said process comprising the steps of (a) enzymatically hydrolysing the cellulosic material with a combination of a first whole fermentation broth comprising cellulolytic and/or hemicellulolytic enzymes produced by culturing a filamentous fungus in the presence of an inducer and a second whole fermentation broth comprising cellulolytic and/or hemicellulolytic enzymes produced by culturing a filamentous fungus in the absence of an inducer to obtain the sugar product and (b) optionally, recovering the sugar product. In a preferred embodiment step (a) is done with a mixed whole fermentation broth obtainable by a process for producing a mixed whole fermentation broth as described herein and comprising a cellobiohydrolase I, a cellobiohydrolase II, an endoglucanase, a beta-glucosidase, an endoxylanase, a lytic polysaccharide monooxygenase and an acetyl xylan esterase. The mixed whole fermentation broth obtainable by a process for producing a mixed whole fermentation broth as described herein may also comprise a beta-xylosidase.

Herein is also described a process for the preparation of a sugar product from cellulosic material, said process comprising the steps of (a) enzymatically hydrolysing the cellulosic material with a mixed whole fermentation broth obtainable by a process for producing a mixed whole fermentation broth comprising cellulolytic and/or hemicellulolytic enzymes as described herein and comprising a cellobiohydrolase I, a cellobiohydrolase II, an endoglucanase, a beta-glucosidase, an endoxylanase, a lytic polysaccharide monooxygenase and an acetyl xylan esterase to obtain the sugar product, and (b) optionally, recovering the sugar product. The mixed whole fermentation broth obtainable by a process for producing a mixed whole fermentation broth as described herein may also comprise a beta-xylosidase.

Herein is also described a process for the preparation of a sugar product from cellulosic material, said process comprising the steps of (a) enzymatically hydrolysing the cellulosic material with a mixed whole fermentation broth comprising cellulolytic and/or hemicellulolytic enzymes obtainable by a process to obtain a mixed whole fermentation broth as described herein, and (b) optionally, recovering the sugar product.

Herein is also described a process for the preparation of a sugar product from cellulosic material, said process comprising the steps of (a) enzymatically hydrolysing the cellulosic material with a mixed whole fermentation broth that is obtained by (i) culturing a filamentous fungus in the presence of an inducer to produce a first whole fermentation broth comprising cellulolytic and/or hemicellulolytic enzymes, (ii) culturing a filamentous fungus in the absence of an inducer to produce a second whole fermentation broth comprising cellulolytic and/or hemicellulolytic enzymes, and (iii) combining the first and second whole fermentation broth to produce the mixed whole fermentation broth comprising cellulolytic and/or hemicellulolytic enzymes, to obtain the sugar product, and (b) optionally, recovering the sugar product.

Herein is also described a process for the preparation of a sugar product from cellulosic material, said process comprising the steps of (i) culturing a filamentous fungus in the presence of an inducer to produce a first whole fermentation broth comprising cellulolytic and/or hemicellulolytic enzymes, (ii) culturing a filamentous fungus in the absence of an inducer to produce a second whole fermentation broth comprising cellulolytic and/or hemicellulolytic enzymes, (iii) combining the first and second whole fermentation broth to produce a mixed whole fermentation broth comprising cellulolytic and/or hemicellulolytic enzymes, (iv) enzymatically hydrolysing the cellulosic material with the mixed whole fermentation broth to obtain the sugar product, and (v) optionally, recovering the sugar product.

Herein is also described a process for the preparation of a sugar product from cellulosic material, said process comprising the steps of (i) culturing a filamentous fungus in the presence of an inducer to produce a first whole fermentation broth comprising cellulolytic and/or hemicellulolytic enzymes, said culturing being done in a first broth production container, (ii) culturing a filamentous fungus in the absence of an inducer to produce a second whole fermentation broth comprising cellulolytic and/or hemicellulolytic enzymes, said culturing being done in a second broth production container, wherein the second broth production container is optionally co-located with the first broth production container, (iii) optionally, transporting the first and/or second whole fermentation broth comprising cellulolytic and/or hemicellulolytic enzymes to a mixed broth production container, (iv) combining the first and second whole fermentation broth to produce a mixed whole fermentation broth comprising cellulolytic and/or hemicellulolytic enzymes, said combining being done in the mixed broth production container, wherein the mixed broth production container is optionally co-located with the first broth production container and/or the second broth production container, (v) optionally, transporting the mixed whole fermentation broth comprising cellulolytic and/or hemicellulolytic enzymes to a sugar production container, (vi) enzymatically hydrolysing the cellulosic material with the mixed whole fermentation broth comprising cellulolytic and/or hemicellulolytic enzymes to obtain the sugar product, said enzymatically hydrolysis being done in the sugar production container, wherein the sugar production container is optionally co-located with the first broth production container and/or the second broth production container and/or the mixed broth production container, and (vii) optionally, recovering the sugar product.

Herein is also described a process comprising the steps of (i) culturing a filamentous fungus in the presence of an inducer to produce a first whole fermentation broth comprising cellulolytic and/or hemicellulolytic enzymes, said culturing being done in a first broth production container, (ii) culturing a filamentous fungus in the absence of an inducer to produce a second whole fermentation broth comprising cellulolytic and/or hemicellulolytic enzymes, said culturing being done in a second broth production container, wherein the second broth production container is optionally co-located with the first broth production container, (iii) combining the first and second whole fermentation broth to produce a mixed whole fermentation broth comprising cellulolytic and/or hemicellulolytic enzymes, said combining being done in a mixed broth production container, wherein the mixed broth production container is optionally co-located with the first broth production container and/or the second broth production container, and (iv) optionally, providing the mixed whole fermentation broth comprising cellulolytic and/or hemicellulolytic enzymes to a sugar production container for use in a process for enzymatically hydrolyzing cellulosic material with the mixed whole fermentation broth to obtain a sugar product, wherein the sugar production container is optionally co-located with the first broth production container and/or the second broth production container and/or the mixed broth production container.

Herein is also described a process comprising the steps of (i) culturing a filamentous fungus in the presence of an inducer to produce a first whole fermentation broth comprising cellulolytic and/or hemicellulolytic enzymes, said culturing being done in a first broth production container, (ii) culturing a filamentous fungus in the absence of an inducer to produce a second whole fermentation broth comprising cellulolytic and/or hemicellulolytic enzymes, said culturing being done in a second broth production container, wherein the second broth production container is optionally co-located with the first broth production container, (iii) providing the first and second whole fermentation broth to a mixed broth production container for use in a process of combining the first and second whole fermentation broth to produce a mixed whole fermentation broth comprising cellulolytic and/or hemicellulolytic enzymes and subsequent use of the obtained mixed whole fermentation broth in a process for enzymatically hydrolyzing cellulosic material with the mixed whole fermentation broth to obtain a sugar product. Optionally, the mixed broth production container is co-located with the first broth production container and/or the second broth production container.

Optionally, in any of the processes for producing a sugar product from cellulosic material as described herein the same container is used for steps (i) and (ii). This is the case for example when the first whole fermentation broth is produced first and thereafter the second whole fermentation broth is produced in the same container.

Herein is also described a process for the preparation of a sugar product from cellulosic material, said process comprising the steps of (i) culturing a filamentous fungus in the presence of an inducer to produce a first whole fermentation broth comprising cellulolytic and/or hemicellulolytic enzymes, said culturing being done in a first broth production container, (ii) culturing a filamentous fungus in the absence of an inducer to produce a second whole fermentation broth comprising cellulolytic and/or hemicellulolytic enzymes, said culturing being done in a second broth production container, (iii) enzymatically hydrolysing the cellulosic material with a mixed whole fermentation broth comprising cellulolytic and/or hemicellulolytic enzymes to obtain the sugar product, said enzymatically hydrolysis being done in a sugar production container and said mixed whole fermentation broth being produced by combining the first and second whole fermentation broth comprising cellulolytic and/or hemicellulolytic enzymes, said combining being done in a mixed broth production container, and (iv) optionally, recovering the sugar product. Optionally, the first broth production container is co-located with the second broth production container and/or the mixed broth production container. Optionally, the second broth production container is co-located with the mixed broth production container.

In an embodiment of a process for producing a sugar product from cellulosic material as described herein, the mixed whole fermentation broth may be produced by combining the first and second whole fermentation broth comprising cellulolytic and/or hemicellulolytic enzymes, said combining being done in the sugar production container. For example, the first and second whole fermentation broth may be provided concomitantly (i.e. in the form of a mixed whole fermentation broth) to the cellulosic material or separately or sequentially (i.e. the first and second whole fermentation broth are added separately or sequentially to the cellulosic material and combining takes place within the cellulosic material and not before addition to the cellulosic material).

Herein is also described a process for the preparation of a sugar product from cellulosic material, said process comprising the steps of (i) culturing a filamentous fungus in the presence of an inducer to produce a first whole fermentation broth comprising cellulolytic and/or hemicellulolytic enzymes, said culturing being done in a first broth production container, (ii) culturing a filamentous fungus in the absence of an inducer to produce a second whole fermentation broth comprising cellulolytic and/or hemicellulolytic enzymes, said culturing being done in a second broth production container, (iii) combining the first and second whole fermentation broth to produce a mixed whole fermentation broth comprising cellulolytic and/or hemicellulolytic enzymes, said combining being done in a mixed broth production container, wherein the first broth production container and/or the second broth production container and/or the mixed broth production container are co-located, (iv) transporting the mixed whole fermentation broth comprising cellulolytic and/or hemicellulolytic enzymes to a sugar production container, wherein the sugar production container is not co-located with the first broth production container and/or the second broth production container and/or the mixed broth production container, (v) enzymatically hydrolysing the cellulosic material with the mixed whole fermentation broth to obtain the sugar product, said enzymatically hydrolysis being done in the sugar production container, and (vi) optionally, recovering the sugar product.

Herein is also described a process for the preparation of a sugar product from cellulosic material, said process comprising the steps of (i) culturing a filamentous fungus in the presence of an inducer to produce a first whole fermentation broth comprising cellulolytic and/or hemicellulolytic enzymes, said culturing being done in a first broth production container, (ii) culturing a filamentous fungus in the absence of an inducer to produce a second whole fermentation broth comprising cellulolytic and/or hemicellulolytic enzymes, said culturing being done in a second broth production container, wherein the first broth production container and the second broth production container are co-located, (iii) transporting the first and second whole fermentation broth comprising cellulolytic and/or hemicellulolytic enzymes to a mixed broth production container, wherein the mixed broth production container is not co-located with the first broth production container and the second broth production container, (iv) combining the first and second whole fermentation broth to produce a mixed whole fermentation broth comprising cellulolytic and/or hemicellulolytic enzymes, said combining being done in the mixed broth production container, (v) enzymatically hydrolysing the cellulosic material with the mixed whole fermentation broth to obtain the sugar product, said enzymatically hydrolysis being done in a sugar production container, and (vi) optionally, recovering the sugar product. In an embodiment the sugar production container is co-located with the mixed broth production container. In another embodiment the sugar production container is not co-located with the mixed broth production container Herein is also described a process for the preparation of a sugar product from cellulosic material, said process comprising the steps of (i) culturing a filamentous fungus in the presence of an inducer to produce a first whole fermentation broth comprising cellulolytic and/or hemicellulolytic enzymes, said culturing being done in a first broth production container, (ii) culturing a filamentous fungus in the absence of an inducer to produce a second whole fermentation broth comprising cellulolytic and/or hemicellulolytic enzymes, said culturing being done in a second broth production container, wherein the first broth production container and the second broth production container are not co-located, (iii) transporting the first and/or second whole fermentation broth comprising cellulolytic and/or hemicellulolytic enzymes to a mixed broth production container, wherein the mixed broth production container is optionally co-located with the first broth production container or the second broth production container, (iv) combining the first and second whole fermentation broth to produce a mixed whole fermentation broth comprising cellulolytic and/or hemicellulolytic enzymes, said combining being done in the mixed broth production container, (v) transporting the mixed whole fermentation broth comprising cellulolytic and/or hemicellulolytic enzymes to a sugar production container, (vi) enzymatically hydrolysing the cellulosic material with the mixed whole fermentation broth to obtain the sugar product, said enzymatically hydrolysis being done in the sugar production container, wherein the sugar production container is not co-located with the mixed broth production container, and (vii) optionally, recovering the sugar product.

Herein is also described a process for the preparation of a fermentation product from cellulosic material, comprising the steps of (a) performing a process for the preparation of a sugar product from cellulosic material as described herein, (b) fermenting the sugar product to produce the fermentation product, and (c) optionally, recovering the fermentation product.

In general, in the enzymatic hydrolysis several enzymes are used, i.e. several enzymes with different cellulolytic activities are used. These enzymes can be any of the enzymes described above or any combination thereof. They can be produced by the mixed whole fermentation broth production process as described herein. The fungus can produce only one of these enzymes, but also more than one, i.e. two, three, four or even more enzymes. If not all of the enzymes necessary for the enzymatic hydrolysis are produced by the fungus, the remaining enzymes can be added after culturing to any of the whole fermentation broths. They may also be added to the cellulosic material during enzymatic hydrolysis.

In an embodiment the cellulosic material is lignocellulosic material. In an embodiment the cellulosic material is subjected to at least one solid/liquid separation before or during the enzymatic hydrolysis. In an embodiment the cellulosic material is subjected to pretreatment and at least one solid/liquid separation before or during the enzymatic hydrolysis. The methods and conditions of solid/liquid separation will depend on the type of cellulosic material used and are well within the scope of the skilled artisan. Examples include, but are not limited to, centrifugation, cyclonic separation, filtration, decantation, sieving and sedimentation. During solid/liquid separation, means and/or aids for improving the separation may be used.

In an alternative embodiment, when the enzymatic hydrolysis comprises a separate liquefaction step and saccharification step (as described in more detail below), the product of the liquefaction step can be used in the culturing of the fungus. This can be done with or without addition of enzymatically hydrolysed cellulosic material. Of course, also each and every combination of part of the enzymatically hydrolysed cellulosic material, part of the pretreated cellulosic material, product of the liquefaction step and external carbon and nutrient source can be used in the culturing of the fungus.

In an embodiment the enzymatic hydrolysis comprises at least a liquefaction step wherein the cellulosic material and/or the pretreated cellulosic material is hydrolysed in at least a first container, and a saccharification step wherein the liquefied material is hydrolysed in the at least first container and/or in at least a second container. Saccharification can be done in the same container as the liquefaction (i.e. the at least first container), it can also be done in a separate container (i.e. at least a second container). So, in the enzymatic hydrolysis liquefaction and saccharification may be combined. Alternatively, the liquefaction and saccharification may be separate steps. In an embodiment there is a solid/liquid separation between liquefaction and saccharification.

The enzymatic hydrolysis can be performed in one or more containers but can also be performed in one or more tubes or any other continuous system. This also holds true when the enzymatic hydrolysis comprises a liquefaction step and a saccharification step. The liquefaction step can be performed in one or more containers but can also be performed in one or more tubes or any other continuous system and/or the saccharification step can be performed in one or more containers but can also be performed in one or more tubes or any other continuous system. Examples of containers to be used in the present invention include, but are not limited to, fed-batch stirred containers, batch stirred containers, continuous flow stirred containers with ultrafiltration, and continuous plug-flow column reactors. Stirring can be done by one or more impellers, pumps and/or static mixers.

In an embodiment the cellulosic material and/or the pretreated cellulosic material can be added to the one or more containers used for the enzymatic hydrolysis. In an embodiment the enzymes used in the enzymatic hydrolysis are already present in the one or more containers before the cellulosic material and/or the pretreated cellulosic material is added. In another embodiment the enzymes used in the enzymatic hydrolysis can be added to the one or more containers. In an embodiment the cellulosic material and/or the pretreated cellulosic material is already present in the one or more containers before the enzymes used in the enzymatic hydrolysis are added. In an embodiment both the cellulosic material and/or the pretreated cellulosic material and the enzymes used in the enzymatic hydrolysis are added simultaneously to the one or more containers. The enzymes used in the enzymatic hydrolysis may be an aqueous composition. This paragraph also holds true when the enzymatic hydrolysis comprises a liquefaction step and a saccharification step.

In an embodiment, the total enzymatic hydrolysis time is 10 to 300 hours, 20 to 250 hours, preferably 30 to 200 hours, more preferably 40 to 150 hours.

In an embodiment the enzymatic hydrolysis is done at a temperature from 40° C. to 90° C., from 45° C. to 80° C., from 50° C. to 70° C., from 55° C. to 65° C.

In an embodiment the enzymatic hydrolysis is conducted until 70% or more, 80% or more, 85% or more, 90% or more, 92% or more, 95% or more of available sugar in the lignocellulosic material is released.

In an embodiment oxygen is added during the enzymatic hydrolysis. In an embodiment oxygen is added during at least a part of the enzymatic hydrolysis. Oxygen can be added continuously or discontinuously during the enzymatic hydrolysis. In an embodiment oxygen is added one or more times during the enzymatic hydrolysis. In an embodiment oxygen may be added before the enzymatic hydrolysis, during the addition of cellulosic material to a container used of enzymatic hydrolysis, during the addition of enzyme to a container used of enzymatic hydrolysis, during a part of the enzymatic hydrolysis, during the whole enzymatic hydrolysis or any combination thereof. Oxygen is added to the one or more containers used in the enzymatic hydrolysis.

Oxygen can be added in several forms. For example, oxygen can be added as oxygen gas, oxygen-enriched gas, such as oxygen-enriched air, or air. Examples how to add oxygen include, but are not limited to, addition of oxygen by means of sparging, blowing, electrolysis, chemical addition of oxygen, filling the one or more containers used in the enzymatic hydrolysis from the top (plunging the hydrolysate into the container and consequently introducing oxygen into the hydrolysate) and addition of oxygen to the headspace of said one or more containers. When oxygen is added to the headspace of the container(s), sufficient oxygen necessary for the hydrolysis reaction may be supplied. In general, the amount of oxygen added to the container(s) can be controlled and/or varied. Restriction of the oxygen supplied is possible by adding only oxygen during part of the hydrolysis time in said container(s). Another option is adding oxygen at a low concentration, for example by using a mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the liquid hydrolysis container contents of cellulosic material. It can also be blown into the headspace of the container.

In an embodiment oxygen is added to the one or more containers used in the enzymatic hydrolysis before and/or during and/or after the addition of the cellulosic material and/or the pretreated cellulosic material to said one or more containers. The oxygen may be introduced together with the cellulosic material and/or the pretreated cellulosic material that enters the hydrolysis container(s). The oxygen may be introduced into the material stream that will enter the container(s) or with part of the container(s) contents that passes an external loop of the container(s).

In an embodiment the container(s) used in the enzymatic hydrolysis have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$. In general, the container(s) will be smaller than 3000 $m^3$ or 5000 $m^3$. In an embodiment the enzymatic hydrolysis of the cellulosic material is done in a container having a volume of 10 to 5000 $m^3$.

In case several containers are used in the enzymatic hydrolysis, they may have the same volume, but also may have a different volume. In case the enzymatic hydrolysis comprises a separate liquefaction step and saccharification step the container(s) used for the liquefaction step and the container(s) used for the saccharification step may have the same volume, but also may have a different volume.

In a preferred embodiment enzymatic hydrolysis and fermentation are separate steps.

Alternatively, they may also be combined. Examples include, but are not limited to, separate hydrolysis and fermentation (SHF), simultaneous saccharification and fermentation (SSF), simultaneous saccharification and co-fermentation (SSCF), hybrid hydrolysis and fermentation (HHF), separate hydrolysis and co-fermentation (SHCF), hybrid hydrolysis and co-fermentation (HHCF), and direct microbial conversion (DMC), also sometimes called consolidated bioprocessing (CBP).

In an embodiment the cellulosic material is lignocellulosic material. Cellulosic material suitable for use in the processes as described herein includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane, cane straw, sugar cane bagasse, switch grass, *miscanthus*, energy cane, corn, corn stover, corn husks, corn cobs, corn fiber, corn kernels, canola stems, soybean stems, sweet sorghum, products and by-products from milling of grains such as corn, wheat and barley (including wet milling and dry milling) often called "bran or fibre", distillers dried grains, as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the afore-mentioned singularly or in any combination or mixture thereof. The enzyme used in the process as described herein can extremely effectively hydrolyze cellulosic material, for example corn stover, wheat straw, cane straw, corn fiber and/or sugar cane bagasse, which can then be further converted into a product, such as ethanol, biogas, butanol, a plastic, an organic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials.

In an embodiment the cellulosic material is pretreated before and/or during the enzymatic hydrolysis. Pretreatment methods are known in the art and include, but are not limited to, heat, mechanical, chemical modification, biological modification and any combination thereof. Pretreatment is typically performed in order to enhance the accessibility of the cellulosic material to enzymatic hydrolysis and/or hydrolyse the hemicellulose and/or solubilize the hemicellulose and/or cellulose and/or lignin, in the cellulosic material. In an embodiment, the pretreatment comprises treating the cellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes). For all the above, 1 bar is 100.000 pascals (Pa).

The cellulosic material may be washed. In an embodiment the cellulosic material may be washed before and/or after the pretreatment. The washing step may be performed before and/or after solid/liquid separation of the cellulosic material and/or the pretreated cellulosic material. If performed after the solid/liquid separation, the solid fraction obtained after solid/liquid separation may be washed. The washing step may be used to remove water soluble compounds that may act as inhibitors for the fermentation and/or hydrolysis step. The washing step may be conducted in manner known to the skilled person. Next to washing, other detoxification methods do exist. The pretreated cellulosic material may also be detoxified by any (or any combination) of these methods which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

The pH during the enzymatic hydrolysis may be chosen by the skilled person. In an embodiment the pH during the hydrolysis may be 3.0 to 6.4. Significantly, a process as described herein may be carried out using high levels of dry matter (of the cellulosic material) in the hydrolysis reaction. In an embodiment the dry matter content of the cellulosic material in the enzymatic hydrolysis is from 10%-40% (w/w), 11%-35% (w/w), 12%-30% (w/w), 13%-29% (w/w), 14%-28% (w/w), 15%-27% (w/w), 16%-26% (w/w), 17%-25% (w/w).

As described before, herein described is also a process for the preparation of a fermentation product from cellulosic material, comprising the steps of (a) performing a process for the preparation of a sugar product from cellulosic material as described herein, (b) fermenting the sugar product to produce the fermentation product, and (c) optionally, recovering the fermentation product.

In an embodiment the container(s) used in the fermentation step have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$, at least 3000 $m^3$, at least 3500 $m^3$, at least 4000 $m^3$, at least 4500 $m^3$. In general, the container(s) will be smaller than 5000 $m^3$.

In an embodiment the fermentation step is performed in one or more containers. The fermentation can be done in the same container(s) wherein the enzymatic hydrolysis is performed.

In an embodiment the fermentation is a step in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic material (e.g. 50 g/l xylose, 35 g/l L-arabinose and 10 g/l galactose). For more dilute sugar compositions, the fermentation time may correspondingly be reduced. In an embodiment the fermentation time of the ethanol production step is between 10 and 50 hours for ethanol made out of C6 sugars and between 20 and 100 hours for ethanol made out of C5 sugars. In an embodiment the fermentation time of the succinic acid production step is between 20 and 70 hours.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem, many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment the fermentations are conducted with a fermenting microorganism, e.g. a yeast. In an embodiment of the invention, the alcohol (e.g. ethanol) fermentations of C5 sugars are conducted with a C5 fermenting microorganism. In an embodiment of the invention, the alcohol (e.g. ethanol) fermentations of C6 sugars are conducted with a C5 fermenting microorganism or a commercial C6 fermenting microorganism. Commercially available yeast suitable for ethanol production include, but are not limited to, BIO-FERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an embodiment the alcohol producing microorganism is a microorganism that is able to ferment at least one C5 sugar. Preferably, it also is able to ferment at least one C6 sugar. In an embodiment the application describes a process for the preparation of ethanol from cellulosic material, comprising the steps of (a) performing a process for the preparation of a sugar product from cellulosic material as described above, (b) fermentation of the sugar product to produce ethanol; and (c) optionally, recovery of the ethanol. The fermentation can be done with a microorganism that is able to ferment at least one C5 sugar, e.g. a yeast.

The alcohol producing microorganisms may be a prokaryotic or eukaryotic organism. The microorganism used in the process may be a genetically engineered microorganism. Examples of suitable alcohol producing organisms are yeasts, for instance *Saccharomyces*, e.g. *Saccharomyces cerevisiae*, *Saccharomyces pastorianus* or *Saccharomyces uvarum*, *Hansenula*, *Issatchenkia*, e.g. *Issatchenkia orientalis*, *Pichia*, e.g. *Pichia stipites* or *Pichia pastoris*, *Kluyveromyces*, e.g. *Kluyveromyces fagilis*, *Candida*, e.g. *Candida pseudotropicalis* or *Candida acidothermophilum*, *Pachysolen*, e.g. *Pachysolen tannophilus* or bacteria, for instance *Lactobacillus*, e.g. *Lactobacillus lactis*, *Geobacillus*, *Zymomonas*, e.g. *Zymomonas mobilis*, *Clostridium*, e.g. *Clostridium phytofermentans*, *Escherichia*, e.g. *E. coli*, *Klebsiella*, e.g. *Klebsiella oxytoca*. In an embodiment the microorganism that is able to ferment at least one C5 sugar is a yeast. In an embodiment, the yeast belongs to the genus *Saccharomyces*, preferably of the species *Saccharomyces cerevisiae*. The yeast, e.g. *Saccharomyces cerevisiae*, used in the processes according to the present invention is capable of converting hexose (C6) sugars and pentose (C5) sugars. The yeast, e.g. *Saccharomyces cerevisiae*, used in the processes according to the present invention can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens,* and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/orXKS1-gene; deletion of the aldose reductase (GRE3) gene; overexpression of PPP-genes TAL1, TKL1, RPE1 and RKl1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

Alternatively, to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

Fermentation products that may be produced by the processes of the invention can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase. In a preferred embodiment an alcohol is prepared in the fermentation processes as described herein. In a preferred embodiment ethanol is prepared in the fermentation processes as described herein.

The processes as described herein may comprise recovery of all kinds of products made during the processes including fermentation products such as ethanol. A fermentation product may be separated from the fermentation broth in manner know to the skilled person. Examples of techniques for recovery include, but are not limited to, chromatography, electrophoretic procedures, differential solubility, distillation, or extraction. For each fermentation product the skilled person will thus be able to select a proper separation technique. For instance, ethanol may be separated from a yeast fermentation broth by distillation, for instance steam distillation/vacuum distillation in conventional way.

EXAMPLES

Example 1

Enzymatic Hydrolysis with Mixed Whole Fermentation Broths

A first whole fermentation broth comprising cellulolytic and hemicellulolytic enzymes was produced by culturing *Rasamsonia emersonii* in the presence of a cellulose inducer according to the methods as described in WO 2011/000949. Furthermore, a second whole fermentation broth comprising cellulolytic and hemicellulolytic enzymes was produced by culturing *Rasamsonia emersonii* overexpressing *Rasamsonia emersonii* beta-glucosidase (described in WO2012/000890) with and without inducer in the fermentation medium according to the methods as described in WO 2011/000949. In case the second whole fermentation broth was produced with inducer, cellulose was used as inducer.

Pretreated cellulosic material (pretreated corn stover) was made by incubating corn stover for 6.7 minutes at 186° C. Prior to the heat treatment, the corn stover was impregnated with $H_2SO_4$ for 10 minutes to set the pH at 2.3 during the pretreatment.

The enzymatic hydrolysis experiments were done in 2 L Scott bottles placed in a shaking incubator at a constant temperature of 62° C. and a shaking speed of 120 rpm. The enzymatic hydrolysis reactions were performed with acid pretreated corn stover (aCS) as prepared above at a final dry matter concentration of 17% w/w and a pH of 4.5. Each enzymatic hydrolysis was done with 500 g reaction mixture per Scott bottle.

At the start of each experiment 43 mg first whole fermentation broth (made with inducer) and 6.6 mg or 3.3 mg second whole fermentation broth (either induced and non-induced) was added per g of pretreated corn stover dry matter. During enzymatic hydrolysis the pH was manually measured by a pH electrode and adjusted to pH 4.5 when needed. Samples were taken for analysis after 144 hours of enzymatic hydrolysis, which were immediately centrifuged for 8 min at 4000×g. The supernatant was filtered over 0.2 µm nylon filters (Whatman) and stored at 4° C. until analysis for sugar content as described below.

The sugar concentrations of the diluted samples were measured using an HPLC equipped with an Aminex HPX-87H column according to the NREL technical report NREL/TP-510-42623, January 2008. The results are shown in Table 1.

TABLE 1

Glucose concentration after 144 h of enzymatic hydrolysis of acid pretreated corn stover by different mixed whole fermentation broths.

| # | Enzyme broth combinations used | Glucose release after 144 hours (in g/L)* |
|---|---|---|
| 1 | 43 mg first whole fermentation broth (induced) + 6.6 mg second whole fermentation broth (induced) | 39.7 |
| 2 | 43 mg first whole fermentation broth (induced) + 6.6 mg second whole fermentation broth (non-induced) | 40.2 |
| 3 | 43 mg first whole fermentation broth (induced) + 3.3 mg second whole fermentation broth (induced) | 39.5 |
| 4 | 43 mg first whole fermentation broth (induced) + 3.3 mg second whole fermentation broth (non-induced) | 39.9 |

*the amount of glucose present in the second fermentation broth (made with and made without inducer) was measured to be <0.01 g/l.

The results in Table 1 clearly show a higher glucose release when mixed whole fermentation broths are used that comprise a combination of an induced and a non-induced whole fermentation broth (see comparison between experiments 1 and 2 and experiments 3 and 4).

The invention claimed is:

1. A process for producing a mixed whole fermentation broth comprising one or more cellulolytic and/or hemicellulolytic enzymes, wherein the process comprises:
    (i) culturing a first filamentous fungus in the presence of an inducer to produce a first whole fermentation broth comprising one or more cellulolytic and/or hemicellulolytic enzymes,
    (ii) culturing a second filamentous fungus in the absence of the inducer to produce a second whole fermentation broth comprising one or more cellulolytic and/or hemicellulolytic enzymes, and
    (iii) combining the first whole fermentation broth and the second whole fermentation broths to produce the mixed whole fermentation broth comprising one or more cellulolytic and/or hemicellulolytic enzymes,
    wherein the first filamentous fungus is different from the second filamentous fungus; and
    wherein the inducer is selected from the group consisting of cellulose, carboxymethylcellulose (CMC), xylan, xylose, gentiobiose, sophorose, lactose, glycerol, glucose, sorbitol, cellobiose, xylobiose, galactose, laminaribiose, maltose, fructose, mannitol, arabinose, arabinitolo, mannose, sorbose, and a mixture of disaccharides prepared from glucose by incubating glucose with a transglycosylating beta-glucosidase or any combination thereof.

2. The process according to claim 1, wherein each of the first filamentous fungus and the second filamentous fungus is selected from the group of genera consisting of Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes pleurotus, Trichoderma and Trichophyton.

3. A process for producing a mixed whole fermentation broth comprising one or more cellulolytic and/or hemicellulolytic enzymes, wherein the process comprises:
    (i) culturing a first filamentous fungus in the presence of an inducer to produce a first whole fermentation broth comprising the one or more cellulolytic and/or hemicellulolytic enzymes,
    (ii) culturing a second filamentous fungus in the absence of the inducer to produce a second whole fermentation broth comprising the one or more cellulolytic and/or hemicellulolytic enzymes, and
    (iii) combining the first whole fermentation broth and the second whole fermentation broths to produce the mixed whole fermentation broth comprising the one or more cellulolytic and/or hemicellulolytic enzymes,
    wherein, the inducer is selected from the group consisting of cellulose, carboxymethylcellulose (CMC), xylan, xylose, gentiobiose, sophorose, lactose, glycerol, glucose, sorbitol, cellobiose, xylobiose, galactose, laminaribiose, maltose, fructose, mannitol, arabinose, arabinitolo, mannose, sorbose, and a mixture of disaccharides prepared from glucose by incubating glucose with a transglycosylating beta-glucosidase or any combination thereof, and
    wherein the mixed whole fermentation broth comprises a ratio of first whole fermentation broth to second whole fermentation broth in a range from 99% (w/w) to 1% (w/w)-70% (w/w) to 30% (w/w).

4. The process according to claim 1, wherein the first whole fermentation broth comprises a cellobiohydrolase I, a cellobiohydrolase II, an endoglucanase, a beta-glucosidase, a beta-xylosidase, an endoxylanase, a lytic polysaccharide monooxygenase, an acetyl xylan esterase or any combination thereof.

5. The process according to claim 1, wherein the second whole fermentation broth comprises a cellobiohydrolase I, a cellobiohydrolase II, an endoglucanase, a beta-glucosidase, a beta-xylosidase, an endoxylanase, a lytic polysaccharide monooxygenase, an acetyl xylan esterase or any combination thereof.

6. The process according to claim 3, wherein the first filamentous fungus is different from the second filamentous fungus.

7. The process according to claim 3, wherein the first filamentous fungus is identical to the second filamentous fungus.

8. The process according to claim 1,
    wherein, when culturing the first filamentous fungus, the inducer is present in an amount from 0.01 (w/v) to 10% (w/v), and
    wherein when culturing the second filamentous fungus, the inducer is present in an amount less than 0.01% (w/v).

9. The process according to claim 3,
wherein, when culturing the first filamentous fungus, the inducer is present in an amount from 0.01 (w/v) to 10% (w/v), and
wherein when culturing the second filamentous fungus, the inducer is present in an amount less than 0.01% (w/v).

* * * * *